(12) United States Patent
Stango et al.

(10) Patent No.: US 9,782,135 B2
(45) Date of Patent: Oct. 10, 2017

(54) X-RAY MAMMOGRAPHY AND/OR BREAST TOMOSYNTHESIS USING A COMPRESSION PADDLE

(71) Applicants: Timothy R. Stango, Sandy Hook, CT (US); Kenneth F. Defreitas, Patterson, NY (US); Ian Shaw, Yorktown Heights, NY (US); Jay Stein, Boston, MA (US); Lynne Jameson-Meehan, Melrose, ID (US); Loren Niklason, North Tetonia, ID (US)

(72) Inventors: Timothy R. Stango, Sandy Hook, CT (US); Kenneth F. DeFreitas, Patterson, NY (US); Ian Shaw, Yorktown Heights, NY (US); Jay Stein, Boston, MA (US); Lynne Jameson-Meehan, Melrose, MA (US); Loren Niklason, North Tetonia, ID (US)

(73) Assignee: Hologic, Inc., Marlborough, MA (US)

( * ) Notice: Subject to any disclaimer, the term of this patent is extended or adjusted under 35 U.S.C. 154(b) by 96 days.

(21) Appl. No.: 14/787,076

(22) PCT Filed: Apr. 24, 2014

(86) PCT No.: PCT/US2014/035334
§ 371 (c)(1),
(2) Date: Oct. 26, 2015

(87) PCT Pub. No.: WO2014/176445
PCT Pub. Date: Oct. 30, 2014

(65) Prior Publication Data
US 2016/0081633 A1   Mar. 24, 2016

Related U.S. Application Data

(63) Continuation-in-part of application No. 13/679,446, filed on Nov. 16, 2012, now Pat. No. 9,332,947.
(Continued)

(51) Int. Cl.
*A61B 6/02* (2006.01)
*A61B 6/04* (2006.01)
*A61B 6/00* (2006.01)

(52) U.S. Cl.
CPC ............ *A61B 6/0414* (2013.01); *A61B 6/025* (2013.01); *A61B 6/04* (2013.01); *A61B 6/502* (2013.01)

(58) Field of Classification Search
CPC ... A61B 6/0421; A61B 6/0414; A61B 6/0435; A61B 5/708; A61B 2019/205; A61B 6/04; A61B 6/025; A61B 6/502
See application file for complete search history.

(56) References Cited

U.S. PATENT DOCUMENTS

| 3,971,950 A | 7/1976 | Evans et al. |
| 4,567,899 A | 2/1986 | Kamens et al. |

(Continued)

FOREIGN PATENT DOCUMENTS

| JP | 2011-206438 A | 10/2011 |
| JP | 2011-206439 A | 10/2011 |
| WO | WO 2014/059366 A1 | 4/2014 |

OTHER PUBLICATIONS

PCT International Search Report in International Application PCT/US2012/065546, mailed Feb. 5, 2013, 4 pgs.
(Continued)

*Primary Examiner* — Sean Luck

(57) ABSTRACT

An x-ray breast imaging system comprising a compression paddle in which the compression paddle comprises a front
(Continued)

wall and a bottom wall. The front wall is configured to be adjacent and face a chest wall of a patient during imaging and the bottom wall configured to be adjacent a length of a top of a compressed breast. The bottom wall extends away from the patient's chest wall, wherein the bottom wall comprises a first portion and a second portion such that the second portion is between the front wall and the first portion. The first portion is generally non- coplanar to the second portion, wherein the compression paddle is movable along a craniocaudal axis. The x-ray breast imaging system also comprises a non-rigid jacket releasably secured to the compression paddle, the non-rigid jacket positioned between the compression paddle and the patient.

22 Claims, 12 Drawing Sheets

Related U.S. Application Data

(60) Provisional application No. 61/561,620, filed on Nov. 18, 2011, provisional application No. 61/816,202, filed on Apr. 26, 2013, provisional application No. 61/950,938, filed on Mar. 11, 2014.

(56) References Cited

U.S. PATENT DOCUMENTS

| | | | |
|---|---|---|---|
| 5,474,072 | A | 12/1995 | Shmulewitz |
| 5,506,877 | A | 4/1996 | Niklason et al. |
| 5,706,327 | A * | 1/1998 | Adamkowski ......... A61B 6/502 378/208 |
| 6,577,702 | B1 | 6/2003 | Lebovic et al. |
| 6,587,578 | B2 | 7/2003 | Godik et al. |
| 6,682,484 | B1 | 1/2004 | Entrekin et al. |
| 6,765,984 | B2 | 7/2004 | Higgins et al. |
| 6,850,590 | B2 | 2/2005 | Galkin |
| 6,968,033 | B2 | 11/2005 | Lebovic et al. |
| 6,974,255 | B1 | 12/2005 | Hixson, Sr. |
| 6,975,701 | B2 | 12/2005 | Galkin |
| 7,123,684 | B2 | 10/2006 | Jing et al. |
| 7,245,694 | B2 | 7/2007 | Jing et al. |
| 7,430,272 | B2 | 9/2008 | Jing et al. |
| 7,489,761 | B2 | 2/2009 | DeFreitas et al. |
| 7,505,555 | B2 | 3/2009 | Hermann et al. |
| 7,512,211 | B2 | 3/2009 | Galkin |
| 7,583,786 | B2 | 9/2009 | Jing et al. |
| 7,639,780 | B2 | 12/2009 | Minyard et al. |
| 7,656,993 | B2 | 2/2010 | Hoernig |
| 7,702,142 | B2 | 4/2010 | Ren et al. |
| 7,742,558 | B2 | 6/2010 | Mertelmeier et al. |
| 7,792,244 | B2 | 9/2010 | DeFreitas et al. |
| 7,822,457 | B2 | 10/2010 | Lokhandwalla et al. |
| 7,831,296 | B2 | 11/2010 | DeFreitas et al. |
| 7,869,563 | B2 | 1/2011 | DeFreitas et al. |
| 8,155,421 | B2 | 4/2012 | Ren et al. |
| 9,332,947 | B2 | 5/2016 | Defreitas et al. |
| 2003/0007597 | A1 | 1/2003 | Higgins et al. |
| 2003/0007598 | A1 | 1/2003 | Wang et al. |
| 2003/0099325 | A1 | 5/2003 | Galkin |
| 2004/0156472 | A1 | 8/2004 | Galkin |
| 2005/0008117 | A1 | 1/2005 | Livingston |
| 2005/0113683 | A1* | 5/2005 | Lokhandwalla ..... A61B 5/0091 600/427 |
| 2005/0113863 | A1 | 5/2005 | Ramzipoor et al. |
| 2006/0050844 | A1 | 3/2006 | Galkin |
| 2006/0165215 | A1 | 7/2006 | Galkin |
| 2007/0280412 | A1 | 12/2007 | Defreitas |
| 2008/0181361 | A1* | 7/2008 | Eldered ................... A61B 6/04 378/37 |
| 2008/0240345 | A1 | 10/2008 | Galkin |
| 2008/0247508 | A1 | 10/2008 | Harrington |
| 2009/0003519 | A1 | 1/2009 | Defreitas |
| 2009/0135997 | A1 | 5/2009 | Defreitas |
| 2009/0175408 | A1* | 7/2009 | Goodsitt .............. A61B 6/0414 378/37 |
| 2013/0051520 | A1 | 2/2013 | Ramsauer |
| 2013/0129039 | A1 | 5/2013 | Defreitas |
| 2015/0282770 | A1 | 10/2015 | Klanian et al. |
| 2016/0242707 | A1 | 8/2016 | DeFreitas et al. |

OTHER PUBLICATIONS

PCT International Search Report and Written opinion in International Application PCT/US2012/065546, mailed Feb. 5, 2013, 10 pgs.

European Supplementary Search Report, in Application 12849236. 0, mailed May 13, 2013.

European Search Report in Application 14727133.2, mailed Feb. 27, 2017, 9 pgs.

International Search Report for International Patent Application No. PCT/US2014/035334 mailed Nov. 12, 2014.

\* cited by examiner

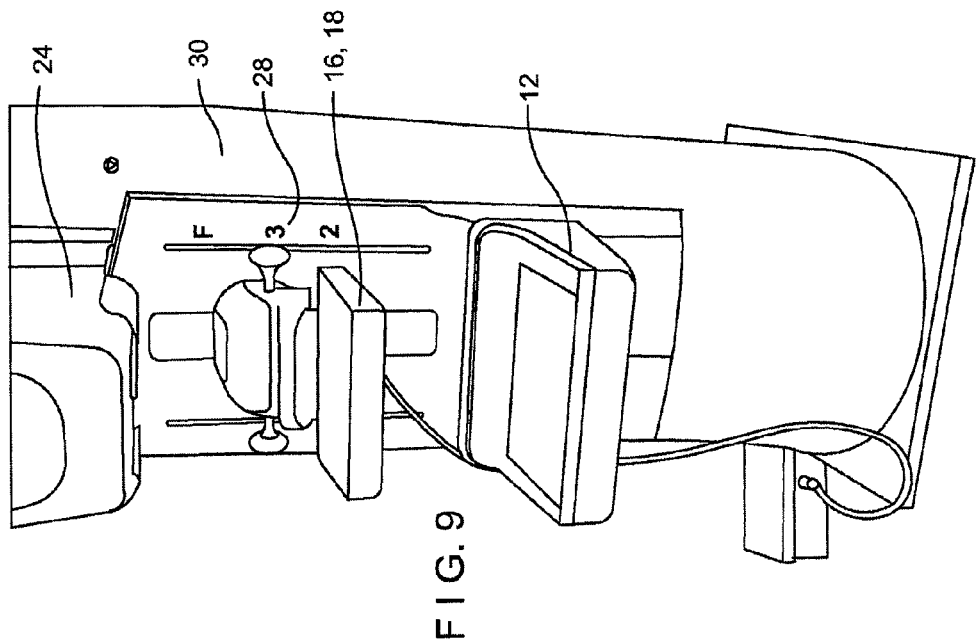
FIG. 7
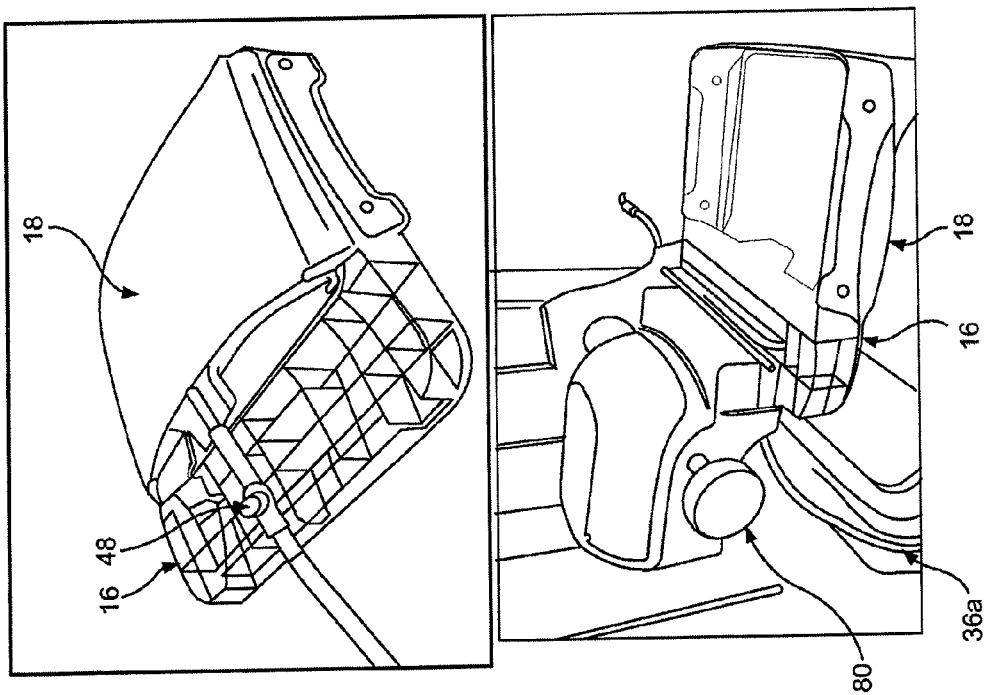
FIG. 8
FIG. 9

X-RAY MAMMOGRAPHY AND/OR BREAST TOMOSYNTHESIS USING A COMPRESSION PADDLE

CROSS-REFERENCE TO RELATED APPLICATIONS

This application is a National Stage Application of PCT/US2014/035334, filed Apr. 24, 2014which claims benefit of U.S. Provisional Patent Application No. 61/950,938, filed Mar. 11, 2014; and U.S. Provisional Patent Application No. 61/816,202, filed Apr. 26, 2013. The present application also claims the benefit under 35 U.S.C. §120 and is a continuation-in-part of U.S. patent application Ser. No. 13/679,446, filed Nov. 16, 2012, now U.S. Pat. No. 9,332,947, which claims the benefit under 35 U.S.C. §119 to U.S. Provisional Patent Application Ser. No. 61/561,620, filed Nov. 18, 2011. The disclosures of each of the foregoing applications are incorporated by reference herein in their entireties. To the extent appropriate, a claim of priority is made to each of the above disclosed applications.

INTRODUCTION

A significant patient concern in x-ray mammography and breast tomosynthesis is the discomfort the patient may feel when the breast is compressed, typically, between two rigid plastic surfaces, with sufficient force to immobilize the breast and spread out the breast tissues for x-ray imaging. One challenge is to ensure that the imaged field includes the desired amount of breast tissue. The reasons for using compression include: (1) to make the breast thinner in the direction of x-ray flux and thereby reduce patient radiation exposure from the level required to image the thicker parts of a breast that is not compressed; (2) to make the breast more uniform in thickness in the direction of x-ray flux and thereby facilitate more uniform exposure at the image plane over the entire breast image; (3) to immobilize the breast during the x-ray exposure and thereby reduce image blurring; and (4) to bring breast tissues out from the chest wall into the imaging exposure field and thus image more tissue. As the breast is being compressed, typically a technician manipulates the breast to position it appropriately and counter the tendency that compression has of pushing breast tissue toward the chest wall and out of the image field.

Standard compression methods for mammography and tomosynthesis use a movable, rigid clear plastic compression paddle in which the surfaces of the paddle are perpendicular to one another. The breast is placed on a breast platform that typically is flat, and the paddle is then compressed onto the breast, usually while a technician or other health professional is holding the breast in place and perhaps manipulates the breast to ensure proper tissue coverage in the image receptor's field of view and to help spread the breast.

One reason for discomfort that the patient may feel is that the compression force is non-uniformly distributed throughout the breast. It is concentrated at the thickest portion of the breast, usually near the chest wall, at or near the lower front edge of the compression paddle and the upper front corner of the breast platform. The anterior portion of the breast, such as near the nipple, may receive less compressive force, or no compression force. The paddle may not even contact this portion of the breast. The terms front, lower and upper pertain to using a CC imaging orientation, with the patient facing the front of the imaging system, although it should be understood that other imaging orientations, including MLO, are used with the same equipment and these terms need to be adjusted accordingly.

Some systems improve patient comfort by providing compression paddles that tilt as the breast is being compressed. A tilting paddle arrangement is available in various paddle sizes from Lorad of Danbury, Conn., a division of the assignee hereof, Hologic, Inc. of Bedford, Mass., under the trade name F.A.S.T. (of FAST). This tilting paddle provides more uniform compression across the breast, and more comfortable breast examinations.

Nonlimiting examples of various approaches to compression paddles and systems therefor include U.S. Pat. Nos. 3,971,950; 5,474,072; 5,506,877 and 6,974,255, U.S. Patent Application Publication Nos. 2005/0008117, 2006/0050844, and 2013/0051520, and Japanese Patent Application Publication Nos. 2011-206438 and 2011-206439. Other methods for improving patient comfort have been proposed and some have been in clinical use to improve patient comfort. One is the use of relatively thin foam pads that are placed above and/or below the breast. The pad deforms to some extent during the compression procedure and may provide improved comfort by spreading out the pressure to a greater extent than using a hard-surfaced paddle and/or breast platform alone. One such pad system is discussed in commonly owned U.S. Pat. Nos. 6,968,033, 6,765,984, 6,577,702, and 7,505,555, and published U.S. Patent Application Publication No. 2003/0007597. Another pad system is proposed in U.S. Pat. Nos. 6,850,590 and 6,975,701 and published U.S. Patent Application Publication Nos. 2006/0050844, US 2004/0156472 and 2003/0099325. Such pads are not transparent to visible light. As a result, if such a pad is between the breast and the compression paddle, the breast will not be visible through the paddle, and this can impair the technician's effort to position and manipulate the breast during compression. The pad needs to be made of fairly dense thin form, so as to provide meaningful deformability when compressed under or above the breast. If the foam pad slips during positioning and as a result does not cover the entire imaging field, an edge of the pad may cause image artifacts.

Another system for improving patient comfort has been proposed for a different purpose—to immobilize the breast during biopsy—by Scientific Biopsy (www.sbiopsy.com). It is understood to use a soft, trough-shaped support to cradle the breast and a flexible band that wraps over the breast to impose a holding force. A thin plastic sheet compressing a breast for ultrasound examination rather than for x-ray imaging is proposed in published patent application US 2003/0007598 (see, e.g., FIG. 7 and paragraph [0115]) but no teaching could be found that the material is transparent to visible light or that the arrangement is useful for x-ray imaging or with a flat breast platform. U.S. Pat. No. 6,682,484 discusses the use of a polymeric membrane stretched under tension to restrain the breast during sonographic and/or x-ray imaging. U.S. Pat. No. 7,822,457 discusses the use of tensioned membrane to compress the breast for medical imaging, and that the membrane may be tensioned with a mechanical device or by means of an inflatable bladder. U.S. Pat. No. 6,587,578 discusses a non-rigid object holder having a resilient membrane attached to a first member to form an inflatable component for holding the object to be examined between the inflatable component and a base support.

Commonly assigned U.S. Pat. Nos. 7,489,761 and 7,792,244 describe (1) placing a fluid-filled pillow or bag between the compression paddle and the breast before the breast is compressed, (2) compressing the breast with a sheet of a material such as Mylar stretched or at least supported between two rods or rollers (instead of using a conventional compression paddle), and (3) using a paddle provided with a lining of concave compressible material.

SUMMARY

It is believed that a need still remains to further improve breast imaging and patient comfort. The present technology is directed to new approaches to address challenges in breast imaging and particularly x-ray breast imaging.

One non-limiting example of such new approaches in mammography and/or breast tomosynthesis involves the use of a specially adapted device to control, distribute and re-direct breast compression forces. Preferably, the device includes a non-rigid jacket for the compression paddle.

In one aspect, the technology relates to: an x-ray breast imaging system having: a compression paddle having: a front wall configured to be adjacent and face a chest wall of a patient during imaging; a bottom wall configured to extend away from the patient's chest wall and to be adjacent a length of a top of a compressed breast, wherein the bottom wall has a central portion and two outer edge portions, wherein the central portion is a non-coplanar with the two outer edge portions, and wherein the compression paddle is movable; and a first axis substantially orthogonal to the front wall. In an embodiment, the two outer edge portions define a reference plane, and wherein the central portion is disposed above the reference plane so as to define a concave surface extending from a first outer edge portion to the central portion to a second outer edge portion. In another embodiment, the compression paddle further has a rear wall disposed opposite the front wall, wherein the central portion of the bottom wall has a pitched surface, wherein a first distance between the central portion and the reference plane proximate the front wall is greater than a second distance between central portion and the reference plane proximate the rear wall. In yet another embodiment, the central portion of the bottom wall is pitched along the first axis from a high point proximate the front wall. In still another embodiment, the system includes a breast platform, wherein the compression paddle is adapted to be disposed in: a compressing position wherein the compressed breast is disposed between the compression paddle and the breast platform; and a non-compressing position wherein the compressed breast is not disposed between the compression paddle and the breast platform, and wherein the bottom wall has a substantially similar contour in both the compressing position and non-compressing position.

In another embodiment of the above aspect, a distance between the central portion and the reference plane is substantially identical in both the compressing position and the non-compressing position. In another embodiment, movement of the compression paddle is selected from a group consisting of movable only along a craniocaudal axis, movable only laterally, and combinations thereof. In yet another embodiment, the system includes an x-ray source selectively emitting an imaging x-ray beam, wherein the x-ray source is configured to move along an arc. In still another embodiment, the x-ray breast imaging system is a breast tomosynthesis x-ray breast imaging system.

In another aspect, the technology relates to: an x-ray breast imaging system having: a compression paddle having a front wall, a bottom wall, and an intermediate portion between the front wall and the bottom wall, the front wall configured to be adjacent and face a chest wall of a patient during imaging and the bottom wall configured to be adjacent a length of a top of a compressed breast, the bottom wall extending away from the patient's chest wall, wherein the intermediate portion is generally non-coplanar to the front wall and the bottom wall, wherein the compression paddle is movable along a craniocaudal axis; and a non-rigid jacket releasably secured to the compression paddle, the non-rigid jacket positioned between the compression paddle and the patient. In an embodiment, the non-rigid jacket is a gel pad jacket. In another embodiment, the intermediate portion has a radius a generally smooth curvature. In another embodiment a height of the intermediate portion is no taller than a height of the bottom wall. In yet another embodiment, a height of the intermediate portion is taller than a height of the bottom wall such that the intermediate portion is closer to the compressed breast relative to the bottom wall. In still another embodiment, the bottom wall has a concave portion and a convex portion relative to the compressed breast.

In another embodiment of the above aspect, the convex portion is where the bottom wall meets the intermediate portion. In another embodiment, the intermediate portion has a curvature having a radius. In yet another embodiment, the front wall is slightly off-angle from vertical. In still another embodiment, movement of the compression paddle is selected from a group consisting of movable only along a craniocaudal axis, movable only laterally, and combinations thereof. In another embodiment, the system includes an x-ray source selectively emitting an imaging x-ray beam, wherein the x-ray source is configured to move along an arc. In another embodiment, the x-ray breast imaging system is a breast tomosynthesis x-ray breast imaging system.

In another aspect, the technology relates to a method of imaging a breast of a patient with x-rays from an x-ray breast imaging including: supporting a bottom of the breast on a breast platform; and compressing the breast by applying a compression paddle system to a top of the breast, the compression paddle system having a paddle having a front wall and a bottom wall and a non-rigid jacket coupled to the paddle, the front wall configured to be adjacent and face a chest wall of a patient during imaging and the bottom wall configured to be adjacent a length of a top of a compressed breast, the bottom wall extending away from the patient's chest wall, wherein the bottom wall has a first portion and a second portion such that the second portion is between the front wall and the first portion, the first portion generally non-coplanar to the second portion, the compression paddle is movable only along a craniocaudal axis, and the non-rigid jacket positioned between the compression paddle and the breast. In an embodiment, the non-rigid jacket is an inflatable jacket. In another embodiment, the method includes positioning a portion of the compressed breast, the portion distal relative to the patient's chest wall, after compressing the breast. In another embodiment, the method includes inflating the inflatable jacket after compressing the breast. In yet another embodiment, the inflatable jacket is inflated with a fluid. In still another embodiment, the method includes moving an x-ray source over an arc and exposing the compressed breast to a plurality of x-ray beams during movement of the arc.

In another embodiment of the above aspect, a height of the second portion is taller than a height of the first portion such that the second portion is closer to the compressed breast relative to the firs portion. In another embodiment, the bottom wall has a concave portion and a convex portion relative to the compressed breast. In another embodiment, the convex portion is where the first portion meets the second portion. In yet another embodiment, the second portion has a curvature having a radius. In still another embodiment, the front wall is slightly off-angle from vertical. In another embodiment, movement of the compression paddle to compress the breast is selected from a group consisting of movable only along a craniocaudal axis, movable only laterally, and combinations thereof.

Still other aspects, embodiments, features and advantages of these exemplary aspects and embodiments, are discussed in detail below. Any feature, advantage, implementation, embodiment, or example may be combined or form a part of any aspect or any embodiments in any manner consistent with at least one of the principles disclosed herein, and references to "an embodiment," "some embodiments," "an alternate embodiment," "various embodiments," "one embodiment," "example," "feature," "advantage," "implementation" or the like are not necessarily mutually exclusive and are intended to indicate that a particular feature, embodiment, structure, or characteristic described may be included in at least one aspect. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the technology. In the figures, each identical or nearly identical component that is illustrated in various figures is represented by a like numeral. For purposes of clarity, not every component may be labeled in every figure. In the figures:

FIG. 7 is a perspective view of an inflatable jacket secured to a compression paddle (upside down).

FIG. 8 illustrates a compression paddle with an inflatable jacket secured thereto, and with the combination secured to a breast imaging system.

FIG. 9 illustrates a breast imaging system using an inflatable jacket over the compression paddle.

DETAILED DESCRIPTION

Except as otherwise noted, the articles "a," "an," and "the" mean "one or more."

Figure 1:
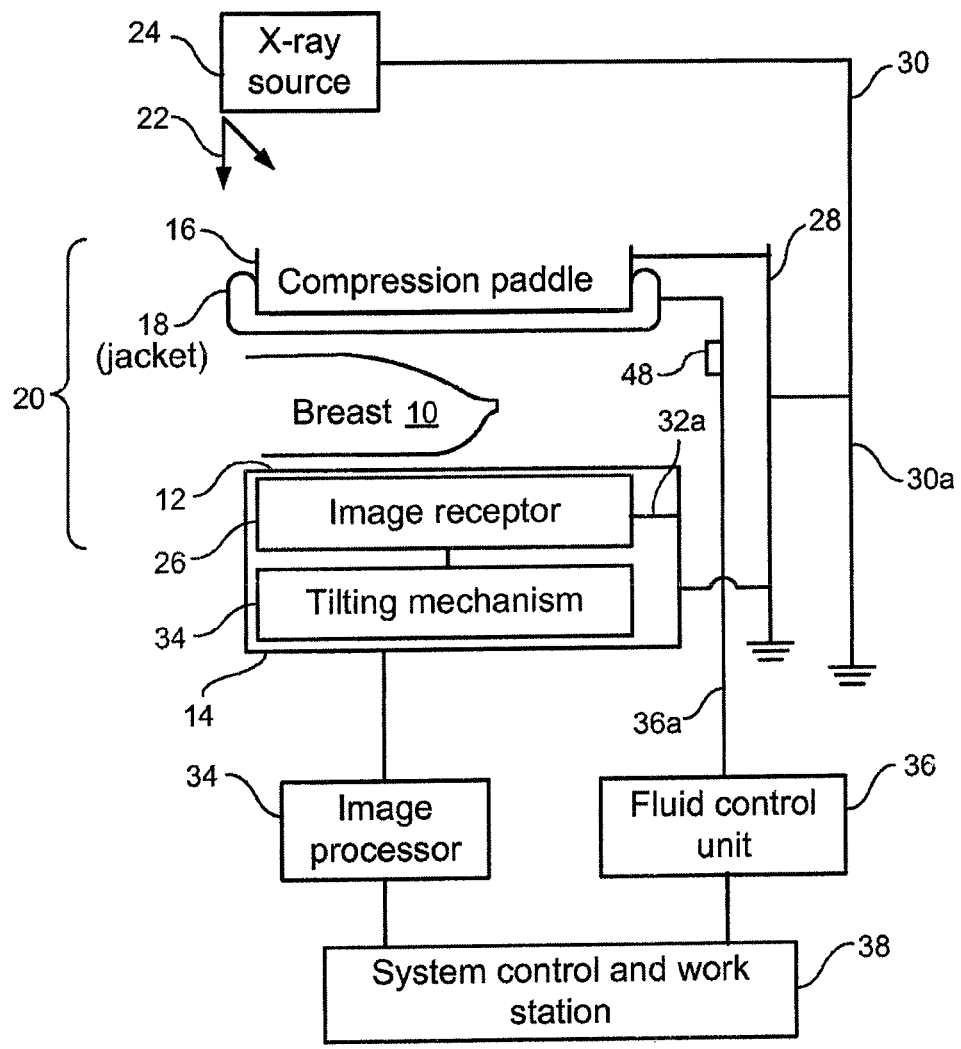
FIG. 1 is a partly schematic view and partly a block diagram of a mammography and/or tomosynthesis system using an inflatable or inflated paddle jacket in imaging a patient's breast with x-rays.
Figure 2:
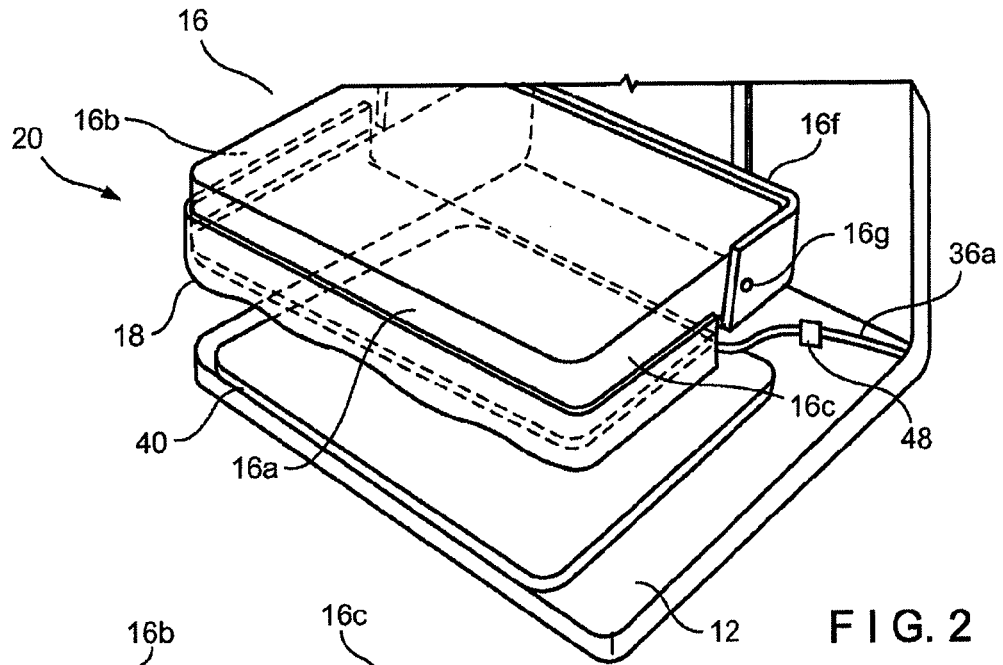
FIG. 2 is a partial perspective view, not to scale, which illustrates a compression paddle provided with an inflatable or inflated jacket and a breast platform with a compressible mat thereon, as a part of an x-ray mammography and/or tomosynthesis system.

Referring to FIG. 1, a patient's breast 10 is immobilized for x-ray imaging between a breast platform 12 and a compression paddle 16. Platform 12 can be the upper surface of a housing 14. At least an underside of compression paddle 16 is covered with a non-rigid paddle jacket, such as, preferably, an inflatable paddle jacket 18. Platform 12 and paddle 16 form a breast immobilizer unit 20 that is in a path of an imaging beam 22 emanating from x-ray source 24. Beam 22 impinges on image receptor 26 that is in housing 14.

Immobilizer 20 and housing 14 are supported on an arm 28. X-ray source 24 is supported on an arm 30. For mammography, support arms 28 and 30 can rotate as a unit about an axis such as at 30a between different imaging orientations such as CC and MLO, so that the system can take a mammogram projection image Mp at each orientation. Image receptor 26 remains in place relative to housing 14 while an image Mp is taken. Immobilizer 20 releases breast 10 for movement of arms 28 and 30 to a different imaging orientation. For tomosynthesis, support arm 28 stays in place, with breast 10 immobilized and remaining in place, while at least source support arm 30 rotates source 24 relative to immobilizer 20 and breast 10 about an axis such as 30a.

The system takes plural tomosynthesis projection images of breast 10 at respective angles of beam 22 relative to breast 10. Concurrently, image receptor 26 may be tilted relative to breast platform 12 in sync with the rotation of source support arm 30. The tilting can be through the same angle as the rotation of course 24, but preferably is through a different angle, selected such that beam 22 remains substantially in the same position on image receptor 26 for each of the plural images Tp. The tilting can be about an axis 32a, which can but need not be in the image plane of image receptor 26.

A tilting mechanism 34, which also is in housing 14 or is otherwise coupled with receptor 24, can drive image receptor 24 in a tilting motion. Axes 20a, 24a and 26a extend left-right as seen in FIG. 1, and may but preferably do not coincide. For tomosynthesis imaging, breast platform 12 can be horizontal or can be at an angle to the horizontal, e.g., at an orientation similar to that for conventional MLO imaging in mammography. The system of FIG. 1 can be solely a mammography system, or solely a tomosynthesis system, or a "combo" system that can perform both mammography and tomosynthesis imaging. An example of such a combo system is been offered by the assignee hereof under the trade name Selenia Dimensions. Nonlimiting examples of such a combo system or a tomosynthesis system are described at U.S. Pat. Nos. 7,869,563; 7,831,296; 7,583,786; 7,430,272;

7,245,694; and 7,123,684. When the system is operated, image receptor 26 produces imaging information in response to illumination by imaging beam 22, and supplies it to image processor 34 for processing to generate breast x-ray images. A fluid control unit 36 connects with inflatable jacket 18 via conduit 36a, preferably through a quick-release snap-on connection 48. A system control and work station unit 38 controls the operation of the system and interacts with a user to receive commands and deliver information including processed-ray images.

Referring to FIGS. 1-6 (which are not to scale) for a more detailed illustration of breast immobilizer 20, compression paddle 16 typically is made of clear plastic and has a front wall 16a, a left side wall 16b, a right side wall 16c, and a bottom wall 16d having an underside 16e. Side walls 16b and 16c are supported by a bracket 16f that in turn is supported by support arm 28 for up-down movement along arm 28. For tilting relative to breast 10, paddle 16 is secured to bracket 16 with pins 16g (only the right pin is visible in FIG. 2) and is spring biased such that as paddle 16 presses against breast 10 the front end of paddle 16 lifts against the biasing force. If desirable, a compressible pad 40 may be placed on platform 12 to increase patient comfort, as is known for system offered by the common assignee. In addition, compression paddle 16 can move left-right as in the current system offered by the assignee under the trade name Selenia Dimensions.

An inflatable jacket 18 is releasably secured to compression paddle 16 and has a front wall 18a, a left side wall 18b, a right side wall 18c, and a bottom 18d having a top wall 18e facing the underside 16e of platform 16 and a bottom wall 18f. Bottom 18d thus includes an inflatable chamber formed between walls 18e and 18f of jacket 18. This chamber 18d is in fluid flow communication with fluid control unit 36 via conduit 36a so it can be selectively inflated and, if desired, selectively deflated, to a desired pressure. A quick connect-release, snap-on connector 48 facilitates convenient connection of chamber 18d to fluid control unit 36 and disconnection from unit 36. If desired the bottom of jacket 18 can be divided into two or more chambers, such as chambers 18h and 18i, by a partition 18g, and separate conduits and connect/disconnect device (not shown) can be provided for each so that the two or more chambers can be inflated to desired pressures that may differ from each other.

Jacket 18 can be releasably secured to paddle 16 in any number of ways such that it can be easily attached and removed from paddle 16 and so that it will not undergo undesirable shifts relative to paddle 16 or the patient's skin while the breast is being immobilized and imaged.

Figure 3:
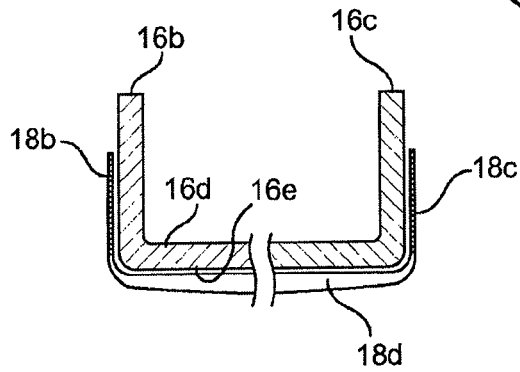
FIG. 3 illustrates schematically a section of the compression paddle with a paddle jacket secured thereto.

FIG. 3 illustrates one example, in which at least some of the surfaces of jacket 18 that face platform 16 are made of or coated with a material that adheres to platform 16 with a force that is sufficiently high to substantially prevent undesirable movement between platform 16 and jacket 18 but also sufficiently low to allow for easy removal of jacket 18 from paddle 16. Preferably at least the upper wall 18e of jacket 18 is made sticky for that purpose, but any one or more of the other walls can also be made sticky instead of or in addition to wall 16e. In this example of using adhesion to releasably secure jacket 18 to paddle 16, the front and side walls of jacket 18 preferably are shorter than the corresponding walls of paddle 16 but in the alternative can be the same height or even taller. The walls of jacket 18 can but need not be the same height; for example front wall 18a can have a lesser height compared with side walls 18b and 18c.

Figure 4:
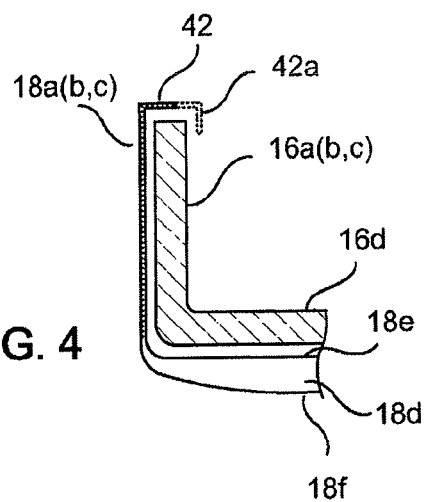
FIG. 4 illustrates schematically two examples of ways to releasably secure a paddle jacket to a compression paddle.

FIG. 4 illustrates other examples of releasably securing jacket 18 to paddle 16. In this example, at least one but preferably two or all three of front wall 18a and side walls 18b and 18c are provided with clipping members 42 that clip over the top of the respective wall of platform 16 and thus keep jacket 18 and platform 16 secured to each other. Clipping member 42 can be as shown in solid lines, or it can have an extension 42a as shown in dashed line. Jacket 18 typically is made of a plastic material such as vinyl that is somewhat stretchable and is dimensioned for a tight fit over platform 16 such that mechanical friction and perhaps some electrostatic force and inherent stickiness of the jacket material combine to maintain the jacket and platform from undesirable movement with respect to each other, but jacket 18 can still be easily peeled from paddle 16 by an operator so that a new jacket can be installed for the next patient if desired. Other examples are contemplated, such as snap connections between the side walls of the jacket and the compression paddle, or other mechanical connections.

Figure 5:
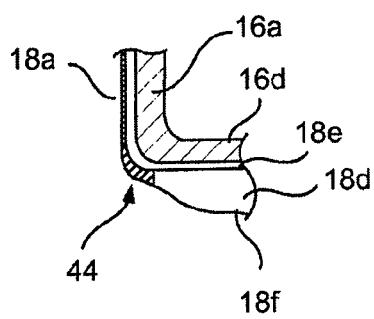
FIG. 5 illustrates schematically a seam in the paddle jacket.

Jacket 18 can be made of two layers of a material such a vinyl similar in chemical composition and thickness to that used for colostomy bags and even kitchen food bags and freezer bags. Preferably the two layers are fused or adhered to each other at the front and side walls of jacket 18, but not at the bottom 18d of jacket 18. Preferably, a seam 44 is formed, e.g., with adhesive material or by fusing, joining the two layers where jacket 18 adjoins the junction of the front and underside of platform 16 when jacket 18 is secured to platform 16, as illustrated in FIG. 5. Seam 42 can extend partly over front wall 16a and partly over underside 16e of platform 16, as illustrated (not to scale) in FIG. 5. Preferably, seam 42 is positioned such that the inflatable volume 18d of jacket 18 does not extent forward beyond front wall 16a of platform 16, so as not to push patient tissue away from platform 16.

Figure 6:
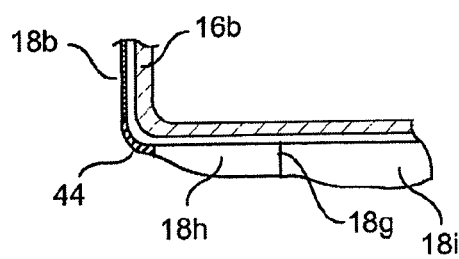
FIG. 6 illustrates a variant in which the bottom of the jacket has multiple chambers that can be pressurized to different degrees.
Figure 10A:
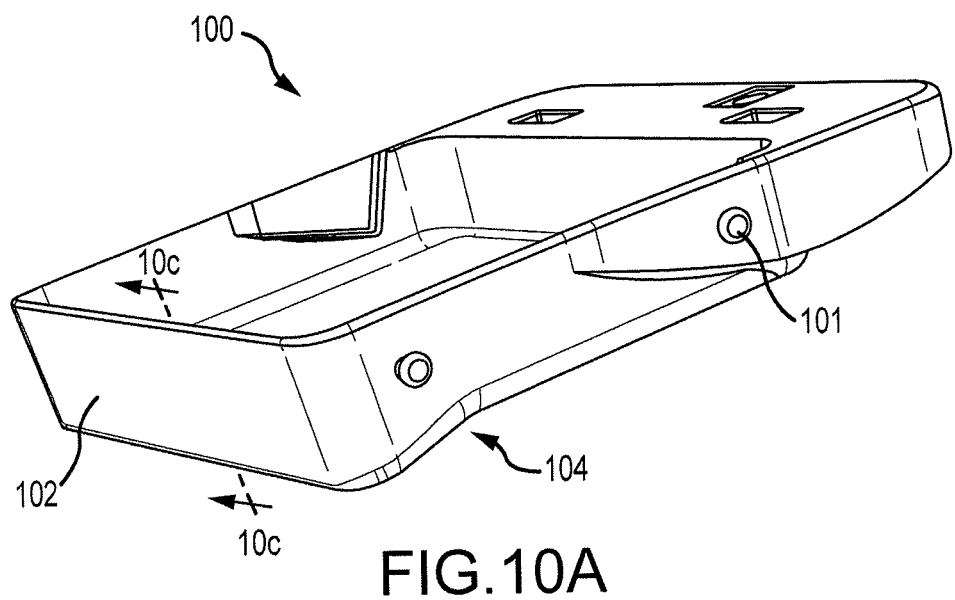
FIGS. 10A-10E illustrate schematic perspective, side, partial cross-section, top, and bottom view, respectively, of a compression paddle according to an embodiment of the present technology.
Figure 10B:
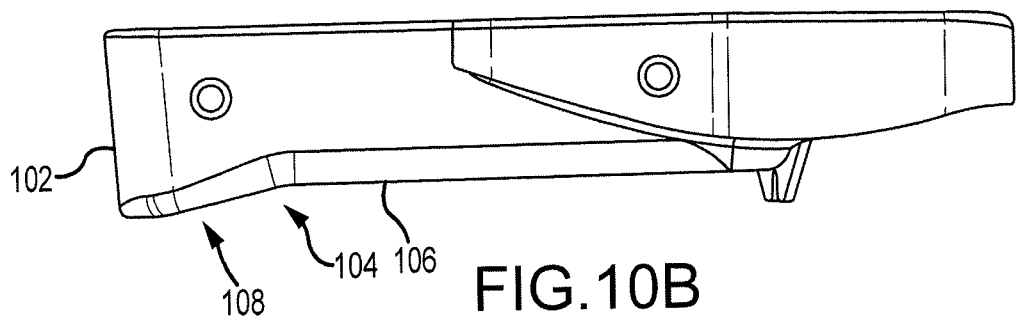
Figure 10C:
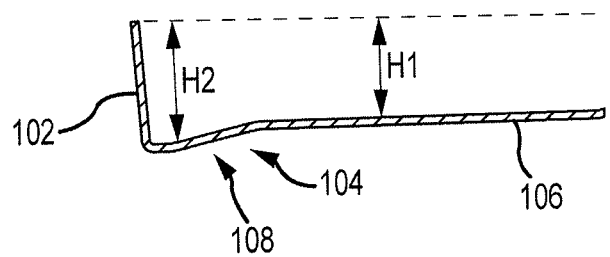
Figure 10D:
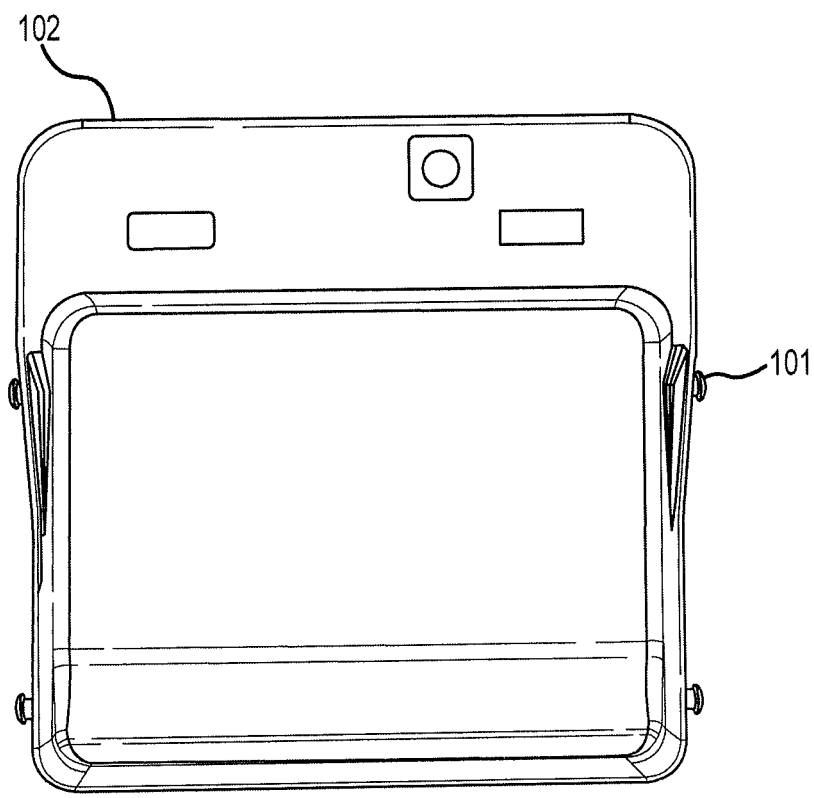
Figure 10E:
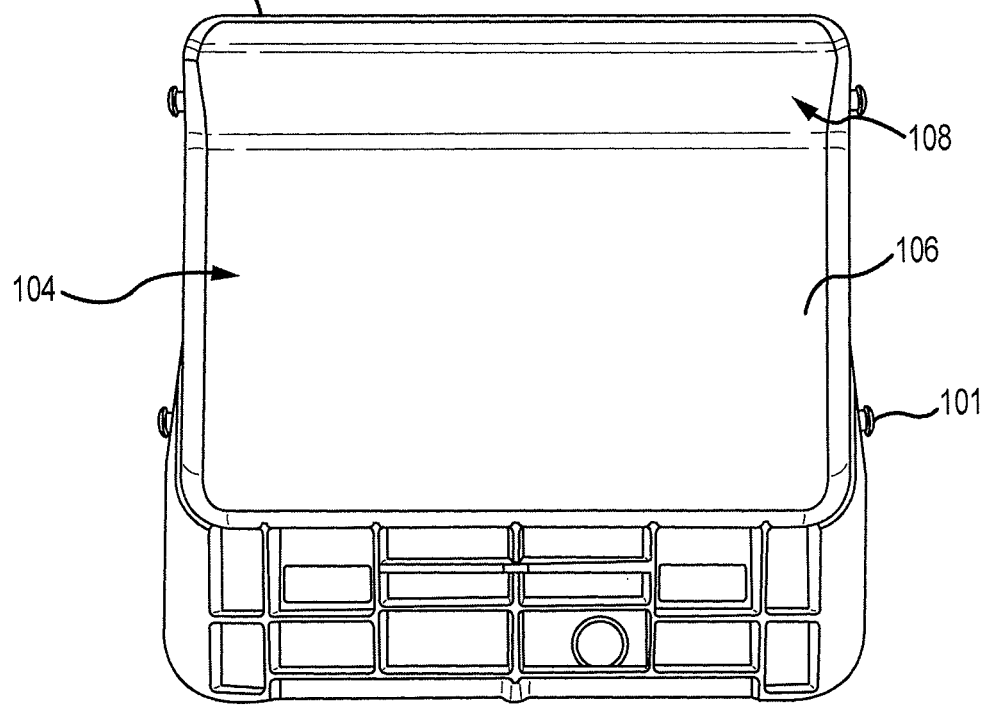
Figure 11A:
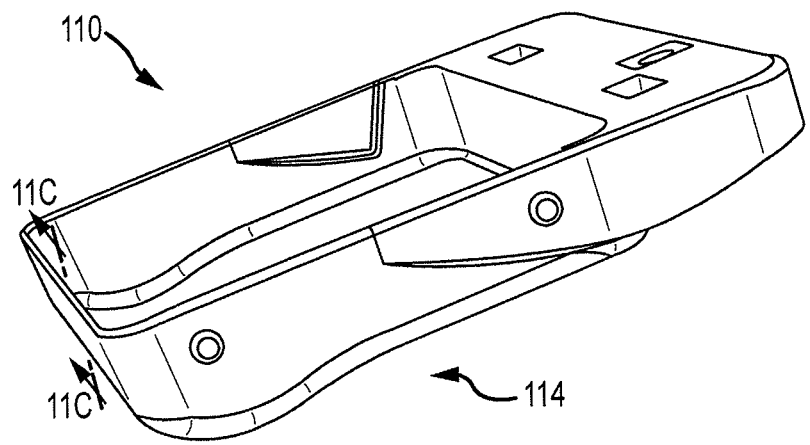
FIGS. 11A-11E illustrate schematic perspective, side, partial cross-section, top, and bottom view, respectively, of a compression paddle in accordance with an embodiment of the present technology.
Figure 11B:
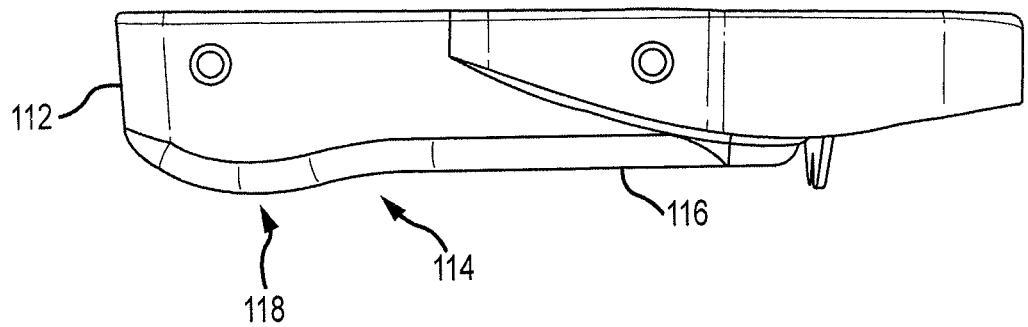
Figure 11C:
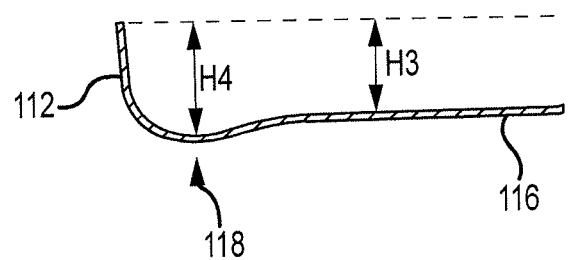
Figure 11D:
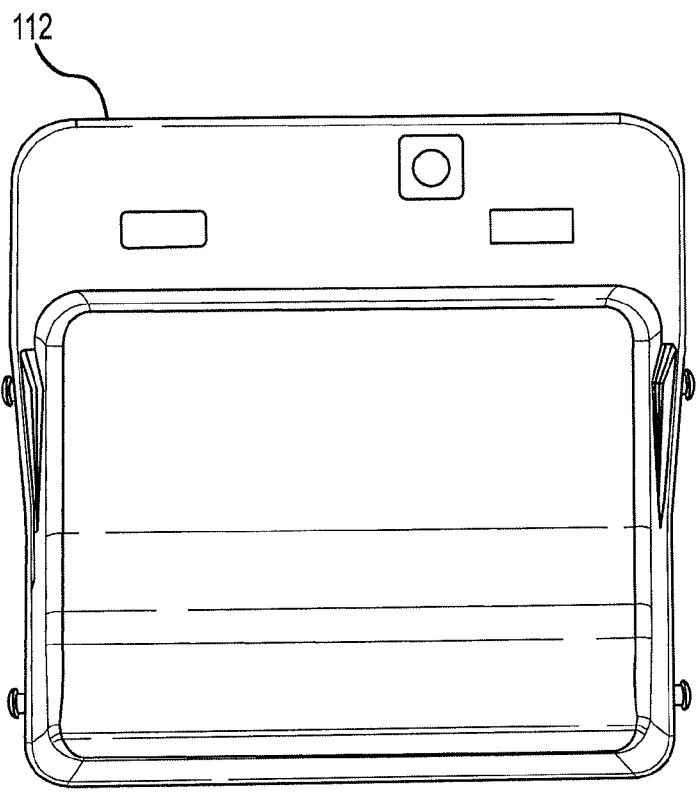
Figure 11E:
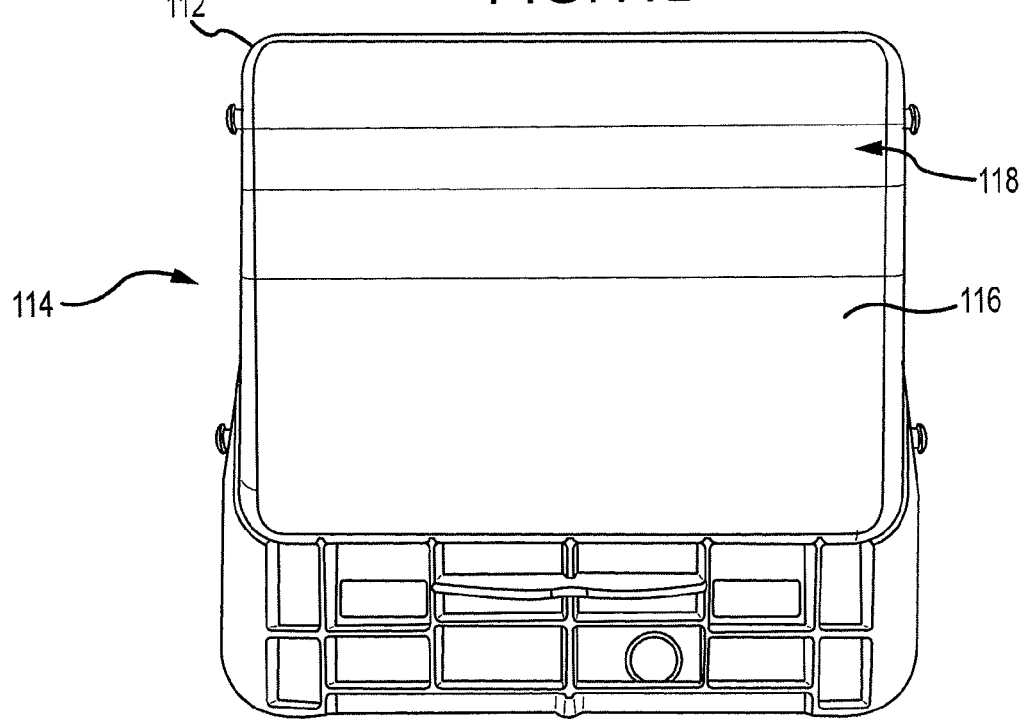
Figure 12A:
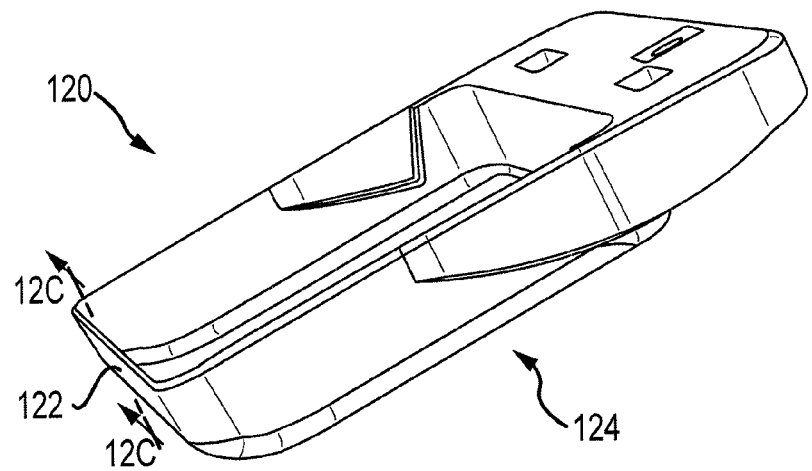
FIGS. 12A-12E illustrate schematic perspective, side, partial cross-section, top, and bottom view, respectively, of a compression paddle according to an embodiment of the present technology.
Figure 12B:
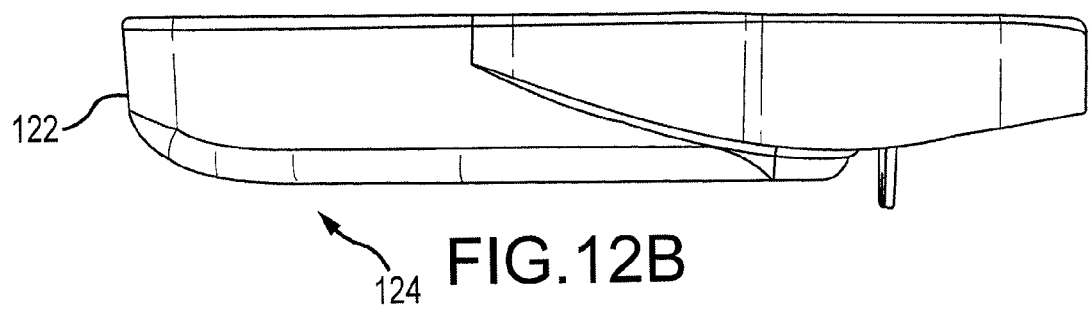
Figure 12C:
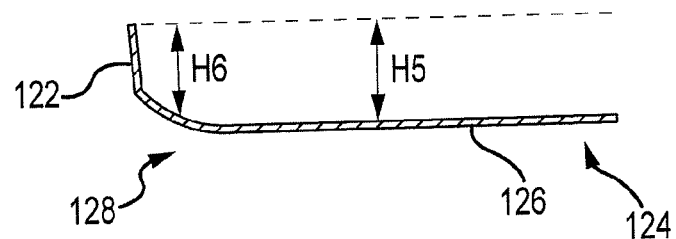
Figure 12D:
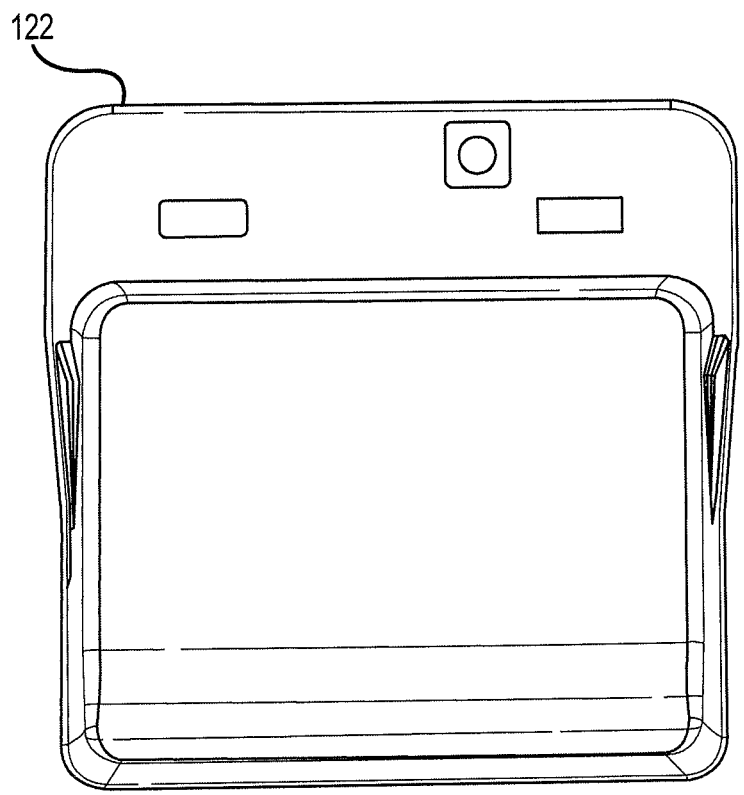
Figure 12E:
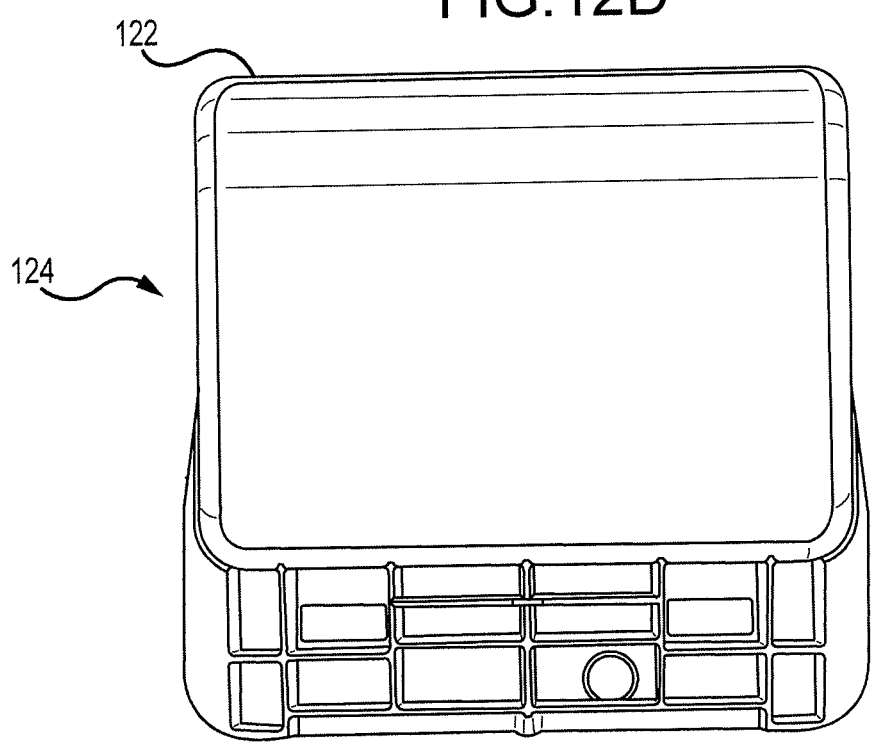

Referring to FIG. 6, the jacket's chamber 18d can have two or more sub-chambers, such as shown at 18h and 18i, each with a respective connection through a snap-on connector and a conduit to fluid control unit 36, so that each subchamber can be inflated to a desired pressure level under operator control or automated system control.

Fluid control unit 36 can be powered by an operator, using a hand-pump or a foot pump and appropriate manual or foot-controlled valves. Alternatively, electric or fluid-powered pumps can be used, with appropriate valves and interfaces such as buttons or switches that the operator controls. As another alternative, fluid control unit 36 can be fully automated such that inflation/deflation of jacket 18 is under control of station 38, when so enabled by an operator, and in response to events such as compression paddle 16 reaching a certain position relative to the patient's breast or to platform 12 or exerting a specified pressure on the patient's breast. The controls over inflation/deflation can be a part of or at least associated with unit 38. In use, the mammography and/or tomosynthesis system is operated as known, for example as known for the systems offered by the common assignee under the commercial designations Selenia and Selenia Dimensions, except for the addition of inflatable paddle jacket 18. Thus, before patient imaging, a jacket 18 is secured to paddle 16 and connected to conduit 36 through a snap-on connector 48. With patient's breast 10 on platform 12 or pad 40, the technician lowers paddle 16 (with jacket 18 secured thereto) to begin compressing breast 10, while manually manipulating the breast to spread out breast tissue and pull tissue away from the patient's chest wall and into the x-ray field of view. In this process, the technician may control the degree of inflation of the jacket's chamber 18d before and/or after paddle 16 has been lowered to its final desired position by adding to and/or releasing fluid from chamber 18*d*. If chamber 18*d* has two or more sub-chambers, the technician may individually control the inflation of each in a similar manner. Once the technician or other health professional is satisfied with the position of breast 10, x-ray imaging can commence in a mammography and/or tomosynthesis mode, for example as known for said systems offered by the common assignee.

FIGS. 7-9 illustrate examples of an inflatable or inflated jacket 18 secured to a compression paddle in a breast imaging system. In FIG. 7, jacket 18 and paddle 16 are upside-down to better illustrate them and quick-release coupling 48. FIG. 8 illustrates paddle 16 and jacket 18 in a more typical orientation, and also illustrates a knob 80 that can be manually turned to move paddle 16 and its support left-right. FIG. 9 illustrates in perspective view a system in which components are identified by reference numeral used in FIG. 1 and described in connection with FIG. 1.

While specific examples have been described above, it should be clear that variations thereof are within the scope of the technology defined by the appended claim. As one of many possible examples, a similar inflatable jacket can be used on or over breast platform 12 in addition to or instead of using jacket 18 on compression paddle 16. In that example, such a jacket can be similarly secured to housing 14, or it can omit the side walls so that only a chamber similar to chamber 18*d* (or multiple sub- chambers) is present on breast platform 12, possibly with a front wall similar to front wall 18*a* but extending down along the front wall of housing 14.

Referring now to FIGS. 10A-10E, an embodiment of a compression paddle 100 is shown. The compression paddle 100 can be used with any of the features described herein, such as a non-rigid paddle jacket (e.g., an inflatable paddle jacket) for use with the x-ray imaging system described above, such as a breast tomosynthesis x-ray imaging system. The compression paddle 100 includes at least one projection 101 extending from a surface of the compression paddle 100. Although four projections 101 are shown, fewer or more can be utilized. The projections 101 mate with corresponding structures, such as channels or apertures, of a non-rigid jacket. In an embodiment, the non-rigid jacket can be an inflatable jacket, thus, having resilient properties when inflated or a gel pad having elastic properties. Additionally or alternatively, a distal end of the projection can be enlarged and have width larger than a proximal stem portion of the projection. The compression paddle 100 also has a front wall 102 and a bottom wall 104. The front wall 102 is configured to be adjacent and face a chest wall of a patient. The bottom wall 104 extends away from the patient's chest wall and faces a length of a compressed breast. The bottom wall includes a first portion 106 and a second portion 108. The first portion 106 is generally non-coplanar to the second portion 108. In an embodiment, the second portion 108 is rotated about 5 degrees to about 20 degrees from the first portion, preferably about 10 degrees to about 15 degrees, and even more preferably about 25 degrees. The generally non-coplanar configuration (e.g., a wedge-shaped configuration) between the first portion 106 and the second portion 108 aids in locking breast tissue at the chest wall and/or creating a vector of force directed away from the chest wall as the inflatable jacket is inflated. That is, the compression paddle of the present technology along with a non-rigid jacket (to form a compression paddle assembly) helps to prevent breast tissue at or near the chest wall to be positioned or slip away and/or out of the bottom wall and, thus, be out of the field of view during imaging. The second portion helps to push or create a surface that has a vector of surface away from the chest wall to maintain breast tissue in the field of view during imaging. This configuration also helps to ensure not only to have breast tissue in the field of view, but also to maintain more uniform compression of the breast without having pressure or pinch points to a patient which may cause patient discomfort. In an embodiment, the first portion is generally straight and the second portion is generally straight. Alternatively, the first portion can include a first section and a second section in which the first section is generally non-coplanar to the second section and, optionally, the first section is generally straight and the second section is generally straight. The front wall 102 is understood to be the height of the compression paddle 100. In an embodiment, the first portion 106 and the second portion 108 have different heights relative to the top of the front wall. As a nonlimiting example, a height (H1) of the first portion 106 is less than a tallest height (H2) of the second portion 108. Additionally or alternatively, a height (H1) of the first portion 106 can be generally constant (i.e., horizontal) and a height (H2) of the second portion 108 can vary, e.g., linearly or non-linearly. In an embodiment, the front wall 102 is vertical. In another embodiment, the front wall 102 is slightly off-angle from vertical, such as when the compression paddle is applied to the breast. Where a front wall of a compression paddle is off-angle from vertical, such a front wall facilitates in extending further into the chest wall in comparison to a known flat compression paddle.

To compress a breast, a compression paddle assembly of the present technology, having a compression paddle and a non-rigid jacket, is applied to the breast for a first compression. The compression paddle assembly is applied to the breast in a craniocaudal direction. Additionally or alternatively, the compression paddle assembly can move solely in a craniocaudal direction, by tilting the compression paddle assembly, by laterally moving the compression paddle assembly, or combinations thereof. Where the compression paddle assembly is laterally movable, the assembly is movable under manual control or when motorized, optionally, under software control. The assembly can shift automatically depending on the view of the breast to be acquired. As the height of the first portion is less than a height of the second portion, under the first compression, the second portion can be in contact with breast tissue while there can be a clearance between the breast tissue and the first portion. A technologist or technician can further position at least a portion of the breast tissue during the first compression. In one embodiment, the non-rigid jacket can become resilient, e.g., by inflating an inflatable jacket, to place the breast under compression via a second compression. In another embodiment, the non-rigid jacket can be a gel pad which becomes resilient when placed in compression against breast tissue.

Referring now to FIGS. 11A-11E, another compression paddle 110 of the present technology is shown in which a bottom wall 114 has a first portion 116 and a second portion 118. The first portion 116 is generally non-coplanar to the second portion 118 in this configuration and the second portion 118 has a generally smooth curvature. In an embodiment, the second portion 118 is generally concave. Relative to the top of the front wall, the first portion 116 has a height (H3) less than a tallest height (H4) of at least a portion of the second portion 118. In this configuration, the radius of the second portion 118 is about 1.5 inches to about 3.5 inches, preferably about 2.5 inches. The enlarged radius of the second portion 118, e.g., larger than usual, is intended to improve chest wall comfort by, for example, having a generally smooth patient contacting contour. According to an embodiment, the height (H3) of the first portion is generally constant, whereas the height (H4) of the second portion varies. Additionally or alternatively, the shape of the second portion 118 can be generally a smooth curve or other curvilinear shape. A front wall 112 can be vertical or slightly off-angle from vertical when the compression paddle is applied to a breast.

FIGS. 12A-12E illustrate an embodiment of a compression paddle 120 of the present technology. The compression paddle 120 has a front wall 122 and a bottom wall 124. The front wall can be generally vertical or slightly off-angle to vertical when the compression 120 is applied to a breast. The bottom wall 124 includes a first portion 124 and a second portion 128 in which the second portion is an intermediate portion between the front wall and the first portion. The first portion is generally horizontal having a generally constant height (H5) relative to the top of the front wall of the compression paddle 120. A tallest height (H6) of the intermediate portion is no greater than the height (H5) of the first portion. In an embodiment, the height (H6) of the intermediate portion varies, e.g., in a linear fashion, has a generally smooth curvature, or is generally curvilinear. In such a configuration, the shape of the intermediate portion relieves pulling of tissue at the chest wall of a patient. The compression paddle 120 can be used to compress a breast as part of a compression paddle assembly with a non-rigid paddle jacket, preferably a gel pad paddle jacket. Thus, in alternative embodiment, where a gel pad paddle jacket is utilized with the compression paddle 120, there are not two compression steps. The compression paddle assembly would be applied to the breast in one downward motion. Additionally or alternatively, the technologist or technician could but preferably would not be manipulating the breast tissue upon compression.

Figure 13A:
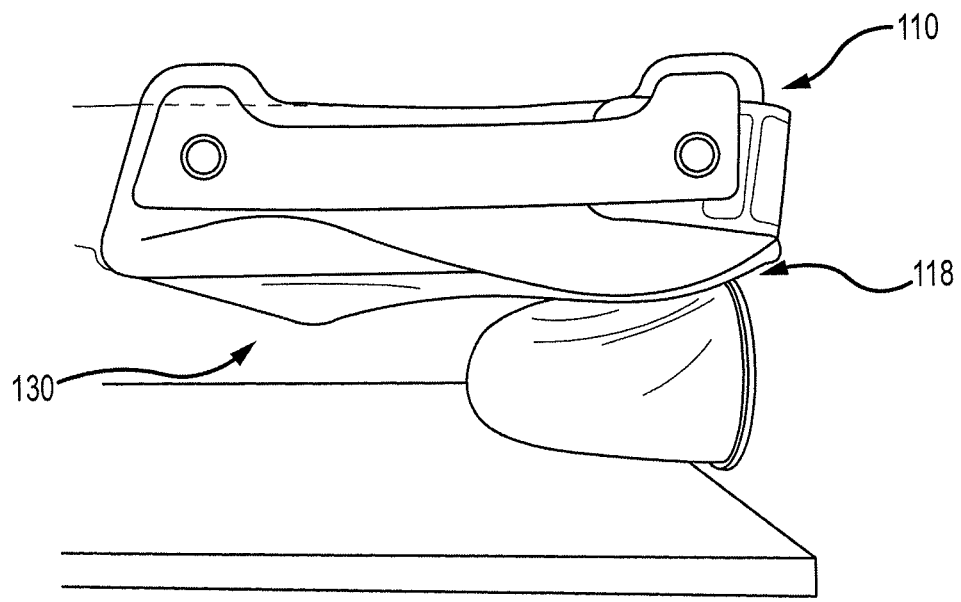
FIGS. 13A-13B illustrate schematic side views a method of breast compression in accordance with an embodiment of the present technology.
Figure 13B:
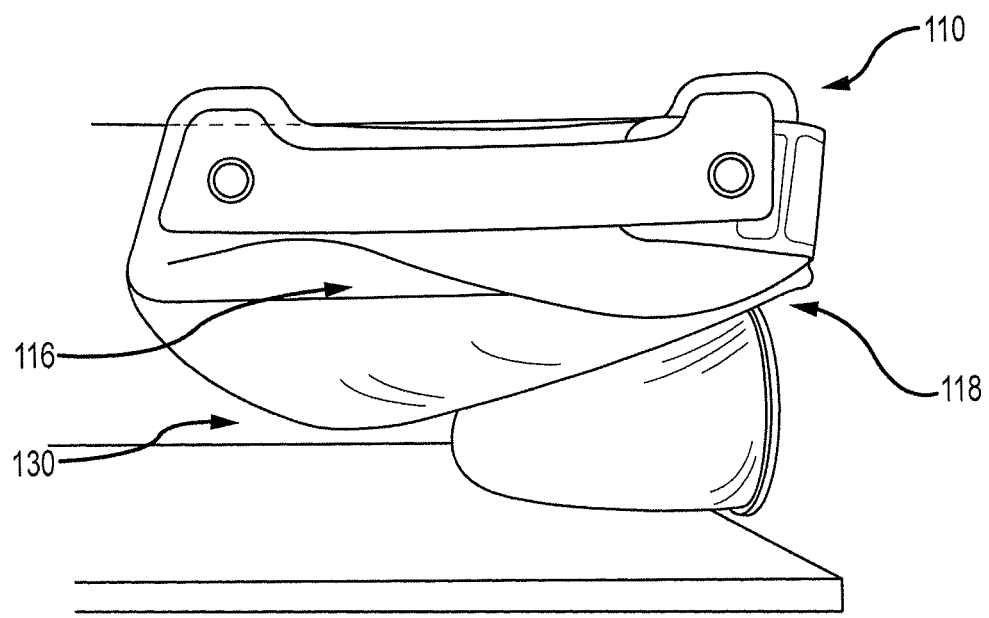

Referring now to FIGS. 13A-13B, a method of compressing a breast using a compression paddle assembly of the present technology is shown. For purposes of illustration, the compression paddle 110 of FIGS. 11A-11E is shown, though any other compression paddle described herein can be used. The method includes at least positioning a breast on a breast platform, positioning the compression paddle assembly relative to the breast, immobilizing the breast by lowering the compression paddle assembly or compressing the breast with the compression paddle assembly, and, optionally, inflating the paddle jacket 130 where an inflatable paddle jacket is utilized. Where applicable, lowering the compression paddle assembly or compression the breast initially with the compression paddle assembly applies a first amount of force on the breast. Inflating a paddle jacket applies an additional amount of force on top of the first amount to aid in compressing the breast evenly for x-ray imaging, e.g., by evenly distributing the force over the top surface of the breast.

Shown as an example in FIGS. 13A-13B, though any of the compression paddles described herein can be used, the breast platform extends laterally up to the front wall of the compression paddle, such as up to the bottom part of the front wall. In an alternative embodiment, the breast platform extends laterally up to where the front wall contacts the chest wall of a patient, in configurations in which the front wall of the compression paddle is tilted or off-angle. The breast platform does not just extend only up to where the first portion ends or is no longer generally horizontal and parallel to the breast platform. This configuration helps to minimize how much of the breast tissue is out of the field of view. Where portions of breast tissue are not in the field of view and/or are pinched (e.g., due to thick and/or dense breast by the chest wall) by the front wall, second portion, and/or portion between the front wall and second portion of the compression paddle, image processing techniques can be utilized to account for such potential distortions. Optionally, image processing techniques can be utilized in any event as tissue by the chest wall can often be dense and/or thick. With known flat compression paddles, such compression paddles need to compress breast tissue significantly from anterior to posterior to try to get as much breast tissue into the field of view as much as possible. Compression paddles of the present technology are configured such that not as much compression force can be needed to image breast tissue, thus, potentially leading to a more comfortable mammogram. Preferably, the compression paddles of the present technology apply about 25% to about 50% less compression force than that of a known flat compression paddle, as measured from the output signal of a load cell located behind where the compression paddle mounts to the imaging system (i.e., the paddle mount).

Figure 14A:
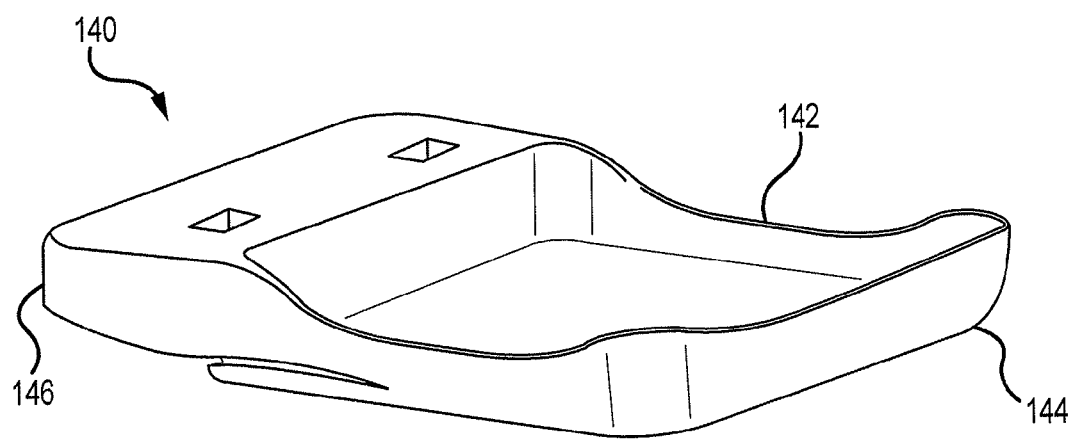
FIGS. 14A-14C illustrate schematic perspective and bottom views of a compression paddle according to an embodiment of the present technology.
Figure 14B:
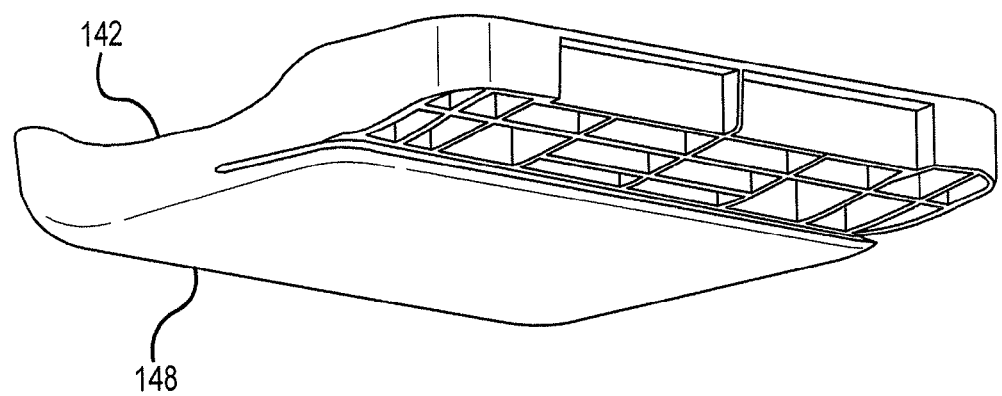
Figure 14C:
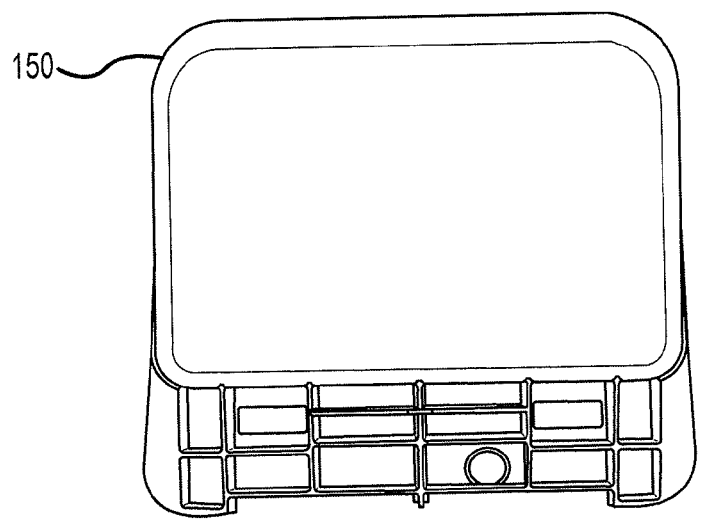

Referring now to FIGS. 14A-14C, shown is another embodiment of a compression paddle 140 of the present technology. In particular, FIGS. 14A-14C illustrate modifications to the compression paddle of FIGS. 12A-12E, though such modifications can be made to any of the compression paddles described herein. Shown in FIGS. 14A-14C are generally rounded corners about the front wall to the bottom of the compression paddle and generally rounded corners about the front wall to the side wall. Compression paddle 140 includes modifications to facilitate greater flexibility and greater conformity to breast tissue. Side walls 142 have a height lower about a portion between the front wall 144 and rear wall 146 than that of the height of the front wall 144 and/or rear 146, e.g., lower by about 20% to about 80%, preferably about 25% to about 50%. Having a side wall with a lower portion facilitates for articulation of the compression paddle 140 at the front wall 144. The compression paddle 140 may also, optionally, include slots formed near the rear corners to facilitate more flexure of the bottom of the compression paddle, as well as the compression paddle 140 overall. Additional optional modifications to increase the flexibility of the compression paddle 140 include varying the thickness of the paddle (e.g., with a portion of the bottom of the compression paddle being thicker than other portions, such as the middle portion having a thickness greater than the portions closer to the side walls) and manufacturing the compression paddle 140 from more flexible materials from known compression paddles (e.g., preferably made with materials that are about 40% more flexible). In the example in which the middle portion of the bottom surface is thicker than the portions closer to the side walls, the thicker, middle portion helps to keep the compression paddle 140 from wrapping around the front of the breast, which can lead to problems with pain at the nipple, pushing the breast toward the chest wall, and pushing the breast potentially off of the detector; having the portion of the bottom surface closer to the side walls be thinner than the middle portion may facilitate more support in the MLO position and may help the compression paddle 140 conform better to a breast shape. Such a configuration may allow better compression in the axilla area and the inframammary fold. The compression paddle 140 can be used to compress a patient's breast with or without an inflatable jacket and/or a gel pad.

Figure 15A:
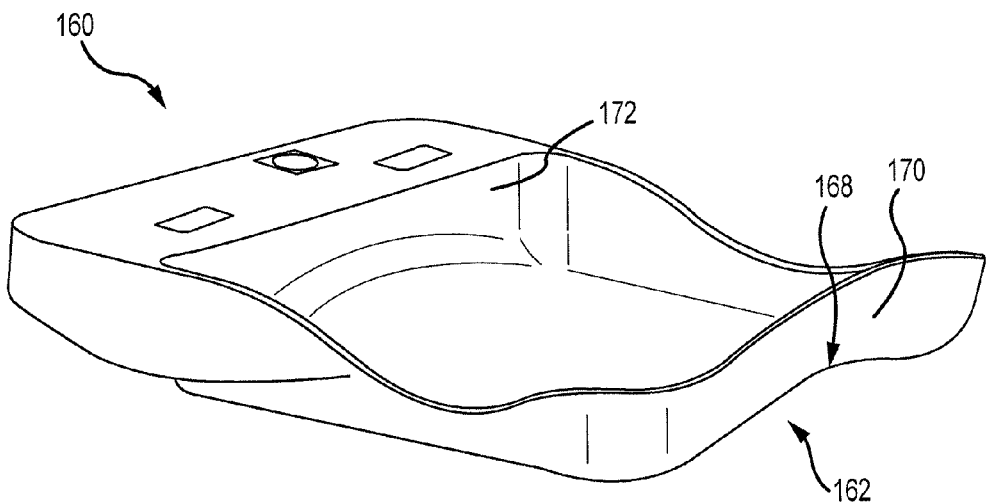
FIGS. 15A-15C illustrate schematic perspective, front, and side views of a compression paddle in accordance with an embodiment of the present technology.
Figure 15B:
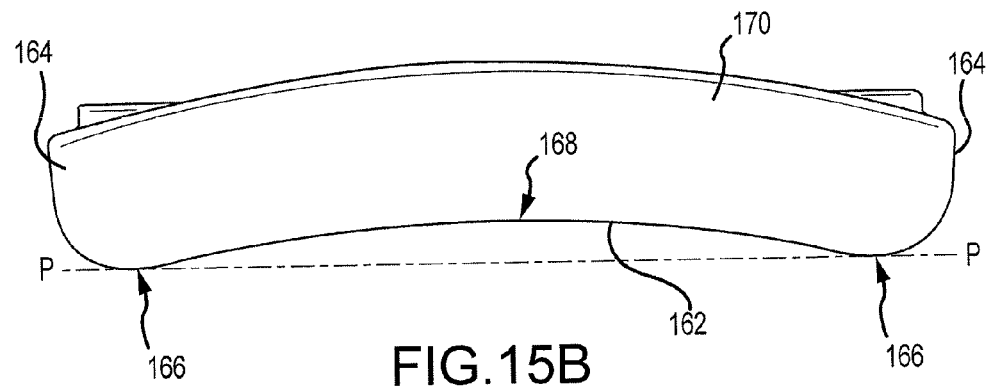
Figure 15C:
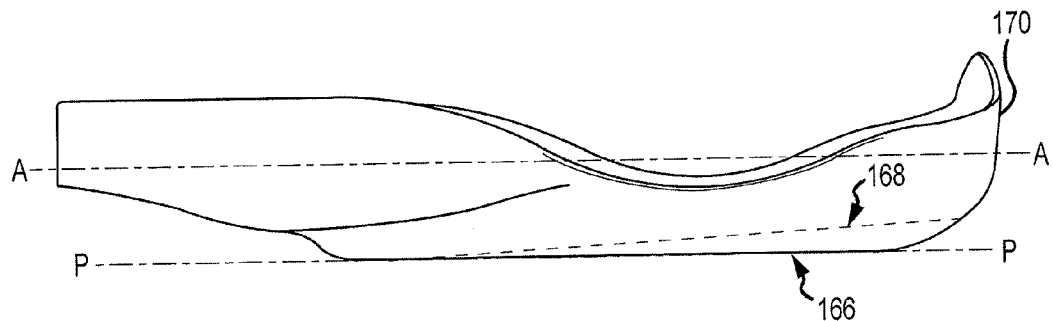

Shown in FIGS. 15A-15C are additional features to a compression paddle 160 of the present technology. The bottom wall of compression paddle 160 includes a generally concave surface 162, which generally may correspond in shape to a breast and/or a compressed breast. The generally concave surface 162 can extend generally between the side walls 164 of the compression paddle 162. Alternatively, a portion of the bottom surface includes a generally concave surface 162, which helps to match the contour of breast tissue. The generally concave surface 162 helps to distribute more equally forces applied to the breast to more closely correspond to the shape of the breast. Such a configuration may help provide more comfort to a patient as the breast is being compressed. The generally concave surface 162 includes two outer edge portions 166 that define a reference plane P, as well as a central portion 168. The central portion 168 is non-coplanar with the outer edge portions 166, such that the central portion 168 is raised relative to or disposed above the reference plane P. The central portion 168 may be level (e.g., parallel to the reference plane P or an axis A of the paddle 160) or may be pitched downward from a front wall 170 to a rear wall 172 of the paddle 160. This may help further conform the paddle 160 to the shape of the breast.

The generally concave surface 162 may also help to prevent the breast from slipping and moving during image acquisition. As an example, this configuration may help prevent slipping of the breast in the MLO position by supporting the breast more, in comparison to known flat compression paddles that often allow the breast to slip during image acquisition. The generally concave surface 162 may have smooth curvature or can have any other shape that is generally concave, e.g., the surface 162 may include ridges, lines, and/or other elements from injection molding the compression paddle 160, the surface may have a generally trapezoidal shape, etc. Additionally or alternatively, the compression paddle 160 can be used to compress a patient's breast with or without an inflatable jacket and/or a gel pad. In another embodiment, the generally concave surface 162 may not be uniformly concave from the front wall 170 (i.e., the chest facing wall) to the rear wall 172. As compressed breast tissue may not extend as far back as the rear wall 172, the concavity may be greater near the front wall 170 compared to the rear wall 172. As an example, the bottom surface 167 may be generally concave near the front wall 170 and may be flatter near the rear wall 172. In an additional or alternative example, the radius of the generally concave surface is greater near the front wall compared to the bottom surface near the rear wall. This non-uniformity may help to provide more even compression from the nipple to the chest wall of the breast.

Generally, the compression paddles of the present technology described herein may be more comfortable to a patient undergoing breast compression during a mammogram or x-ray imaging of the breast. The compression paddles of the present technology described herein generally require less compression force to be applied to accomplish the same tautness as that of a known flat compression paddle. The paddles may be manufactured of substantially rigid or flexible materials. Use of rigid materials allows the paddle to sufficiently compress the breast without deforming. For example, in the embodiment depicted in FIGS. 15A-15C, a distance between the central portion 168 and the referral plane may be substantially the same when the paddle 160 is compressing a breast or not compressing a breast. For example, the concave contour of the bottom wall may be substantially the same. The particular shapes and contours of disclosed herein may reduce or eliminate discomfort during breast compression.

In the embodiments in which a compression paddle utilizes an inflatable bag, a pressure sensor can be utilized to prevent overinflating or underinflating the bag. In alternative embodiments, the volume of the inflatable bag can be calculated with use of syringe. Additionally or alternatively, a motorized setup can be used to inflate the bag, optionally, in which a mechanical component like a lead screw can be used to prevent from overinflating the bag.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

All parts, ratios, and percentages herein, in the Detailed Description and Claims are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All documents cited herein are, in the relevant part, incorporated herein by reference; the citation of any document is not to be construed as an admission that it is prior art with respect to the present technology. To the extent that any meaning or definition of a term or in this written document conflicts with any meaning or definition in a document incorporated by reference, the meaning or definition assigned to the term in this written document shall govern.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the technology. Accordingly, the foregoing description and drawings are by way of example only.

What is claimed is:

1. An x-ray breast imaging system comprising:
a compression paddle comprising:
a front wall configured to be adjacent and face a chest wall of a patient during imaging, wherein the front wall comprises a top;
a bottom wall configured to extend away from the patient's chest wall and to be adjacent a length of a top of a compressed breast, wherein the bottom wall comprises a central portion, two outer edge portions, a first bottom portion distal the front wall, and a second bottom portion disposed between the first bottom portion and the front wall,
wherein the first bottom portion comprises a first portion height from the top and wherein the second bottom portion comprises a second portion height from the top, and
wherein the first portion height is less than the second portion height, and
wherein the compression paddle is movable; and
a first axis substantially orthogonal to the front wall.

2. The x-ray breast imaging system of claim 1, further comprising a breast platform, wherein the compression paddle is adapted to be disposed in:
a compressing position wherein the compressed breast is disposed between the compression paddle and the breast platform; and
a non-compressing position wherein the compressed breast is not disposed between the compression paddle and the breast platform, and wherein the bottom wall comprises a substantially similar contour in both the compressing position and non-compressing position.

3. The x-ray breast imaging system of claim 1, wherein movement of the compression paddle is selected from a group consisting of movable only along a craniocaudal axis, movable only laterally, and combinations thereof.

4. An x-ray breast imaging system comprising:
a compression paddle comprising a front wall having a top, a bottom wall, and an intermediate portion between the front wall and the bottom wall, the front wall configured to be adjacent and face a chest wall of a patient during imaging and the bottom wall configured to be adjacent a length of a top of a compressed breast, the bottom wall extending away from the patient's chest wall, wherein the intermediate portion is generally non-coplanar to the front wall and the bottom wall and comprises an intermediate portion height from the top greater than a bottom wall height from the top, and wherein the compression paddle is movable along a craniocaudal axis.

5. The x-ray breast imaging system of claim 4, further comprising a non-rigid jacket releasably secured to the compression paddle, the non-rigid jacket positioned between the compression paddle and the patient.

6. The x-ray breast imaging system of claim 4, wherein the intermediate portion comprises a radius of a generally smooth curvature.

7. The x-ray breast imaging system of claim 4, wherein a height of the intermediate portion is taller than a height of the bottom wall, as measured from a top of the front wall.

8. The x-ray breast imaging system of claim 4, wherein a height of the intermediate portion is taller than a height of the bottom wall such that the intermediate portion is closer to the compressed breast relative to the bottom wall.

9. The x-ray breast imaging system of claim 4, wherein the bottom wall has a concave portion and a convex portion relative to the compressed breast.

10. The x-ray breast imaging system of claim 9, wherein the convex portion is where the bottom wall meets the intermediate portion.

11. The x-ray breast imaging system of claim 4, wherein the intermediate portion comprises a curvature having a radius.

12. The x-ray breast imaging system of claim 4, wherein the front wall is slightly off-angle from vertical.

13. The x-ray breast imaging system of claim 4, wherein movement of the compression paddle is selected from a group consisting of movable only along a craniocaudal axis, movable only laterally, and combinations thereof.

14. A method of imaging a breast of a patient with x-rays from an x-ray breast imaging comprising:
supporting a bottom of the breast on a breast platform; and
compressing the breast by applying a compression paddle system to a top of the breast, the compression paddle system comprising a paddle having a front wall having a top, and a bottom wall, the front wall configured to be adjacent and face a chest wall of the patient during imaging and the bottom wall configured to be adjacent a length of a top of a compressed breast, the bottom wall extending away from the patient's chest wall, wherein the bottom wall comprises a first portion and a second portion such that the second portion is between the front wall and the first portion, the first portion generally non-coplanar to the second portion, the compression paddle is movable only along a craniocaudal axis, and wherein the first portion comprises a first portion height from the top and wherein the second portion comprises a second portion height from the top that is greater than the first portion height.

15. The method of claim 14, wherein the compression paddle system further comprises a non-rigid jacket positioned between the compression paddle and the breast.

16. The method of claim 15 further comprising positioning a portion of the compressed breast, the portion distal relative to the patient's chest wall, after compressing the breast.

17. The x-ray breast imaging system of claim 1, wherein a transition between the front wall and the second bottom portion is substantially curved.

18. The x-ray breast imaging system of claim 17, wherein the second bottom portion comprises a substantially smooth curvature.

19. The x-ray breast imaging system of claim 1, wherein the first bottom portion is disposed at an angle to the second bottom portion.

20. The x-ray breast imaging system of claim 1, wherein the front wall is substantially vertical.

21. The x-ray breast imaging system of claim 5, wherein the non-rigid jacket is a gel pad jacket.

22. The method of claim 16 further comprising inflating the inflatable jacket after compressing the breast.

* * * * *